United States Patent [19]

Hinnenkamp et al.

[11] Patent Number: 6,031,129

[45] Date of Patent: Feb. 29, 2000

[54] USE OF PENTAVALENT GROUP VA OXIDES IN ACETIC ACID PROCESSING

[75] Inventors: James A. Hinnenkamp; Noel Hallinan, both of Cincinnati, Ohio

[73] Assignee: Quantum Chemical Corporation, Cincinnati, Ohio

[21] Appl. No.: 08/538,561

[22] Filed: Oct. 3, 1995

[51] Int. Cl.[7] .................................................. C07C 51/12
[52] U.S. Cl. ............................................................ 562/519
[58] Field of Search ............................................. 562/519

[56] References Cited

U.S. PATENT DOCUMENTS

| | | |
|---|---|---|
| 3,818,060 | 6/1974 | Forster et al. . |
| 3,939,219 | 2/1976 | Wilkinson . |
| 4,102,920 | 7/1978 | Bartish . |
| 4,190,729 | 2/1980 | Forster . |
| 4,194,056 | 3/1980 | Antoniades . |
| 4,562,284 | 12/1985 | Drent . |
| 4,927,967 | 5/1990 | Wegman . |
| 5,001,259 | 3/1991 | Smith et al. . |
| 5,003,104 | 3/1991 | Paulik et al. . |
| 5,026,908 | 6/1991 | Smith et al. . |
| 5,144,068 | 9/1992 | Smith et al. . |
| 5,189,214 | 2/1993 | Chen et al. . |
| 5,214,203 | 5/1993 | Koyama et al. . |
| 5,281,751 | 1/1994 | Schreck . |
| 5,391,821 | 2/1995 | Koyama et al. . |
| 5,416,237 | 5/1995 | Aubigne et al. . |

FOREIGN PATENT DOCUMENTS

| | | |
|---|---|---|
| 39855 | 12/1993 | Australia . |
| 0031 606 A1 | 7/1981 | European Pat. Off. . |
| 0072 055 A1 | 2/1983 | European Pat. Off. . |
| 0 083 121 A1 | 7/1983 | European Pat. Off. . |
| 0 097 978 A1 | 1/1984 | European Pat. Off. . |
| 0097 978 A1 | 1/1984 | European Pat. Off. . |
| 0 111 949 A1 | 6/1984 | European Pat. Off. . |
| 0 114 703 A1 | 8/1984 | European Pat. Off. . |
| 0114 703 A1 | 8/1984 | European Pat. Off. . |
| 1326014 | 8/1973 | United Kingdom . |

*Primary Examiner*—Paul J. Killos
*Attorney, Agent, or Firm*—Scully, Scott, Murphy & Presser

[57] ABSTRACT

Methanol is converted to acetic acid by reaction with carbon monoxide in the presence of an improved carbonylation system which comprises a rhodium catalyst component and a liquid reaction medium containing water in low levels, acetic acid, methyl iodide, methyl acetate, and at least one pentavalent Group VA oxide wherein the concentration of pentavalent Group VA oxide to rhodium is greater than about 60:1. The present carbonylation system not only increases the yields and reaction rates but also serves to stabilize the rhodium catalyst component in an active form.

30 Claims, 8 Drawing Sheets

USE OF PENTAVALENT GROUP VA OXIDES IN ACETIC ACID PROCESSING

FIELD OF THE INVENTION

The present invention relates to an improved process for the production of acetic acid by carbonylation of methanol or its derivatives such as methyl acetate or methyl iodide in the presence of a carbonylation catalyst system comprising a rhodium-containing component and a liquid reaction medium. More specifically, the present invention relates to a process whereby improved yields and reaction rates as well as catalyst stability can be obtained by introducing at least one pentavalent Group VA oxide to a carbonylation system under low water conditions. The use of a Group VA pentavalent oxide as contemplated in the practice of the present invention leads to high catalyst stability and/or productivity, even at low water conditions, thus allowing rhodium usage rates to remain at commercially acceptable levels as the water concentration is decreased.

BACKGROUND OF THE INVENTION

In recent years, there has been a great deal of industrial emphasis on conducting methanol carbonylation reactions under conditions wherein the water content in the reaction is less than about 14%.

The ability to perform methanol carbonylation reactions at these water levels results in significant economic benefits since equipment costs and energy requirements are reduced. Furthermore, rhodium (Rh) losses are reduced in low water level systems; rhodium typically being a component of traditional carbonylation catalyst systems. And, since rhodium is very expensive, even small reductions in catalyst loss can result in substantial savings. The problem, however, in many prior art carbonylation processes is that as the amount of water in the reaction is reduced, the concentration of the active catalyst species is lowered, the net effect being that the reaction rate decreases.

In order to overcome the aforementioned problems typically associated with low water carbonylation processes, various additives have been introduced into prior art carbonylation catalyst systems the goal being to increase the reaction rate of the carbonylation process at low water levels. In particular, it has been a practice of the prior art to incorporate an alkali metal halide, such as lithium iodide (LiI), in the carbonylation reaction medium to improve the carbonylation reaction rate and product yield. The following references enunciate the current state of the art in methanol carbonylation wherein LiI is added to increase the reaction rate and yield of the process:

U.S. Pat. Nos. 5,214,203 and 5,391,821 both to Koyama et al. provide processes for producing a carboxylic acid, such as acetic acid, by reacting an alcohol or its derivative with carbon monoxide in the presence of a catalyst system which contains a rhodium component, an alkyl halide, water and an iodide salt, such as lithium iodide. The references disclose that when an extremely large amount of an iodide salt (at least 0.3 mol/liter) is incorporated in the reaction solution, the formation of unwanted side products such as methane, can reportedly be controlled with concurrent improvement in the carbonylation rate.

U.S. Pat. No. 5,003,104 to Paulik et al. provides another carbonylation process which adds LiI to the carbonylation reaction in order to improve the reaction rate of the process. Specifically, the Paulik et al. reference is directed to a process for the carbonylation of a carbonylatable reactant, such as alkyl ester, dialkyl ether, alkyl alcohol or olefin, by reacting same with carbon monoxide. More specifically, the reference discloses a carbonylation process wherein the reaction is conducted in the presence of a catalyst system which comprises a rhodium compound and a halogen-containing promoter, at a temperature from about 50° C. to about 400° C. and a CO partial pressure of 1 to about 15,000 psi. A mixture of LiI and $CH_3I$ are among the various halogen-containing promoters disclosed in the reference.

U.S. Pat. Nos. 5,001,259, 5,026,908 and 5,144,068 to Smith et al. relate to processes for the production of acetic acid which comprise reacting methanol with carbon monoxide in a liquid reaction medium containing a rhodium catalyst, water, acetic acid, methyl acetate, lithium iodide and methyl iodide. The object of the Smith et al. references reportedly lies in catalyst stability and reactor productivity as manifested by maintaining in the reaction medium, along with a catalytic-effective amount of rhodium, a finite concentration of water (at least 0.1 weight percent) and methyl acetate and methyl iodide in specified portions.

U.S. Pat. No. 5,281,751 to Schreck provides a process for preparing aliphatic carboxylic acids of the formula RCOOH, wherein R is an alkyl group having 1 to 5 carbon atoms, comprising the catalytic reaction of an alcohol of the formula ROH and carbon monoxide in the presence of a rhodium catalyst, methyl iodide, lithium iodide (at high content), water (at low content, i.e. 0 to 6.5% by weight) and an organic ester of the formula $RCO_2R$, R being defined as above. The process can optionally be carried out in the presence of hydrogen and/or an organic ligand of the formula $ER"_3$ wherein E is nitrogen, phosphorous, arsenic, antimony or bismuth and R" is an organic moiety. The concentration of the organic ligand employed in the reference is from about 50:1 to about 10:1.

U.S. Pat. No. 5,416,237 to Aubigne et al. relates to an improved process for producing acetic acid by carbonylating methanol in the presence of carbon monoxide, a rhodium carbonylation catalyst, methyl iodide, a carbonylation catalyst stabilizer such as LiI, water, methyl iodide, methyl acetate and acetic acid. Specifically, this reference maintains a finite concentration of water, up to about 10% by weight, and a methyl acetate concentration of at least 2% by weight in the liquid reaction composition and recovers acetic acid by passing the liquid reaction composition through a flash zone to produce a vapor fraction which is then passed to a single distillation column. By maintaining the above concentration of water and methyl acetate in the liquid reaction composition, Aubigne et al. reportedly obtains highly pure acetic acid having a water content of less than 1500 ppm and a propionic acid concentration of less than 500 ppm.

In each of the aforementioned references, the water content of the carbonylation reaction is reduced and the reaction rate is maintained by the addition of an alkali metal halide, e.g. LiI, to the reaction. It is, however, suspected that alkali metal halides, such as LiI, promote stress crack corrosion of the reactor vessel. Thus, it would be of great benefit if a process could be developed that reduces the water content in the carbonylation reaction while maintaining catalyst stability and high reaction rates without the need of adding LiI or any other alkali metal halide to the carbonylation reaction system.

SUMMARY OF THE INVENTION

The present invention relates to an improvement in prior art rhodium-catalyzed carbonylations of an alcohol or its derivatives to a carboxylic acid having one carbon atom more than the alcohol. In particular, the instant invention is directed to an improved process for producing acetic acid (HOAc) from methanol ($CH_3OH$) using a carbonylation system that comprises a rhodium-containing component and a liquid reaction medium which contains the ester of the alcohol being carbonylated, the acid product of the carbonylation reaction and a halide derivative of the hydrocarbon corresponding to the alcohol, especially the iodide derivative. Water, in low levels, is also present in the liquid reaction medium of the instant invention. Thus, for example, where methanol is to be carbonylated into acetic acid, the system to which the instant invention has application comprises a rhodium-containing component and a liquid reaction medium that contains methyl acetate, acetic acid, water, and a methyl halide, such as methyl iodide.

Specifically, the improvement to which the instant invention relates involves the introduction into the carbonylation system of at least one pentavalent Group VA oxide of the formula: $R_3M=O$, wherein M is an element from Group VA of the Periodic Table of Elements, such as N, P, As, Sb or Bi; and each R is independently a substituted or unsubstituted alkyl, aryl, aralkyl or alkaryl wherein any of which substituents of the carbon chains may be straight or branched or both, in an amount such that the concentration of the pentavalent Group VA oxide to rhodium is greater than about 60:1.

In practicing the present invention it has been found that the use of a pentavalent Group VA oxide maintains catalyst stability and high levels of productivity—all at low water levels—thus allowing rhodium usage rates to remain at commercially acceptable levels. The term "low water" level, as used herein in describing the instant invention, denotes a concentration of water of from about 0.01 to about 12 weight % which corresponds to a molarity of water of from about $6.2 \times 10^{-3}$ to about 7.5 M. More preferably, the concentration of water is from about 4 to about 9 weight % which corresponds to a molarity of about 2.5 to about 5.6 M.

It is to be emphasized that in the practice of the instant invention the aforementioned results can be obtained without there being any added alkali metal halides, such as LiI, present in the reaction medium. Thus, in one embodiment of the present invention, lithium iodide is not added to the liquid reaction medium. The ability to eliminate these materials without detriment to reaction rates and catalyst stability lends great advantage to the present invention. And, while the instant invention can be beneficially practiced in this fashion, it can also be practiced upon reaction systems that require or otherwise include the use of alkali metal halides such as LiI. Advantageously, however, even where alkali metal halides are a required or desired part of the reaction system, they can in the practice of the present invention, be utilized in significantly less quantities than heretofore conventionally dictated. Thus, the present invention provides a significant improvement over prior art carbonylation processes since it overcomes the problems associated with alkali metal halide addition by permitting the elimination and minimization of said materials without adverse affect to the overall process.

DETAILED DESCRIPTION OF THE PRESENT INVENTION

Figure 1A:
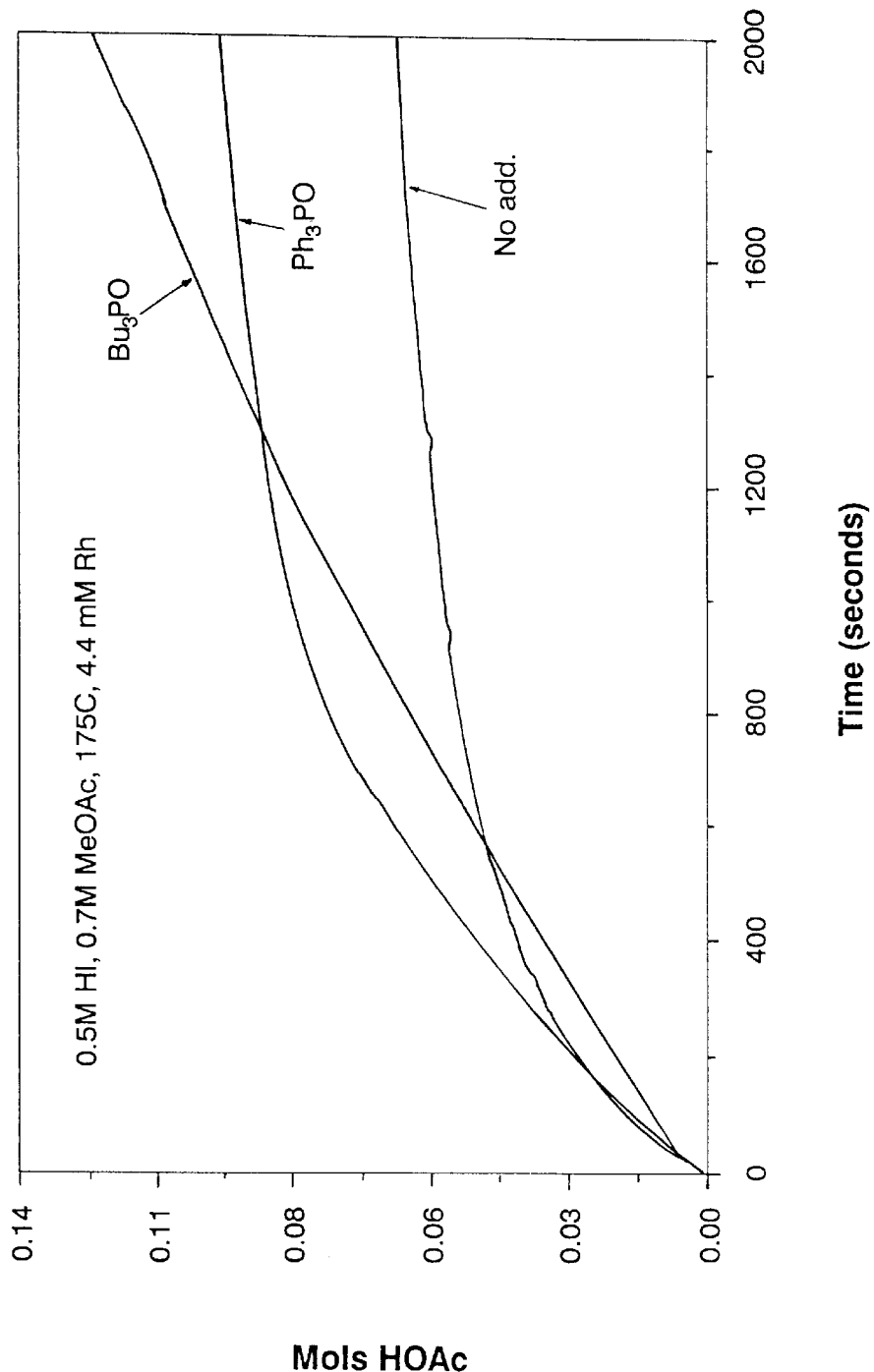
FIGS. 1(a) and (b) represent graphs of the overall rate (a) and initial rate (b) of HOAc production vs. time using the various carbonylation catalyst additives indicated in Examples 1 and 2.

The following description is directed to the carbonylation of methanol or its derivatives to produce acetic acid. However, as indicated hereinabove, the instant invention is also applicable to the carbonylation of higher homologues of methanol, such as ethanol, butanol, pentanol and the like, to produce acids which are higher homologues of acetic acid. The adaptation of the present invention to those other systems will be readily apparent to the artisan given the following discussion.

In accordance with the present invention, improved catalyst stability, as well as improved yields and reaction rates, can be obtained by introducing at least one pentavalent Group VA oxide, as defined hereinbelow, to a carbonylation system which comprises a rhodium-containing component and a liquid reaction medium, which reaction medium contains water, acetic acid, methyl iodide, optionally an alkali metal halide, and methyl acetate. In the practice of the invention, the amount of said pentavalent Group VA oxide is such that its concentration to rhodium is greater than about 60:1. Preferably, the concentration of the pentavalent Group VA oxide to rhodium is from about 60:1 to about 500:1.

Typically, in the instant invention from about 0.2 to about 3 M pentavalent Group VA oxide is present in the liquid reaction medium. More preferably, from about 0.4 to about 1.5 M pentavalent Group VA oxide is present in the liquid reaction medium.

Suitable pentavalent Group VA oxides that can be employed in the instant invention have the formula:

wherein M is an element from Group VA of the Periodic Table of Elements such as N, P, As, Sb or Bi; and each R is independently a substituted or unsubstituted alkyl, aryl, aralkyl, or alkaryl wherein any of which substitutents of the carbon chains may be straight or branched or both.

As employed herein, the alkyl groups, singly or in combination with other groups, contain up to 12 carbon atoms which may be in the normal or branched configuration, including methyl, ethyl, propyl, isopropyl, butyl, isobutyl, t-butyl, amyl, pentyl, hexyl, octyl and the like. The preferred alkyl groups contain 1 to 8 carbon atoms.

The aryl groups are aromatic rings containing from 6 to 14 carbon atoms. Examples or aryl groups include phenyl, α-naphthyl and β-naphthyl, with phenyl being highly preferred.

The aralkyl groups, singly or in combination with other groups, contain up to 16 carbon atoms with each aryl group containing from 6 to 10 carbon atoms and each alkyl group containing up to 6 carbon atoms which may be in the normal or branched configuration. Preferably, each aryl group contains 6 carbon atoms and each alkyl group contains 1 to 3 carbon atoms.

The alkaryl groups, singly or in combination with other groups, contain up to 16 carbon atoms with each alkyl group containing up to 8 carbon atoms which may be in the normal or branched configuration, and each aryl group containing from 6 to 10 carbon atoms. Preferably, each alkyl group contains 6 carbon atoms.

As indicated herein each R group may be substituted or unsubstituted. When R is substituted, it is typically substituted with an alkyl group as defined hereinabove R may also be substituted with other substituents such as halogen, hydroxy, nitro, amino and the like.

In a preferred embodiment of the instant invention, M is phosphorus, and each R is independently either a substituted or unsubstituted alkyl or aryl containing from about 1 to about 6 carbon atoms.

In a most preferred embodiment of the instant invention, at least one R is a substituted or unsubstituted phenyl.

Specific examples of especially preferred pentavalent Group VA oxides that can be used in the instant invention to provide the improved results include, but are not limited to, triethylphosphine oxide, tributylphosphine oxide, tripentylphosphine oxide, diphenylmethylphosphine oxide and triphenylphosphine oxide, with tributylphosphine oxide and triphenylphosphine oxide being more preferred. It should be noted that tributylphosphine oxide is most highly preferred when catalyst stability is the desirable end result and triphenylphosphine oxide is most highly preferred when enhanced rate is the desired goal.

Mixtures of pentavalent Group VA oxides having the foregoing formula are also contemplated within the practice of the present invention.

It is believed that the quantity of pentavalent Group VA oxide employed in the instant invention, as within the strictures of the aforementioned concentration ranges, will maintain the rhodium catalyst in an active form, thus preventing any significant precipitation of the rhodium catalyst during the carbonylation process. By maintaining the rhodium catalyst in an active form, less rhodium is utilized in the carbonylation process. As is well known to those skilled in the art, the active form of rhodium for methanol carbonylations is one which has an oxidation state of I whereas the inactive form of rhodium has an oxidation state of III.

As those skilled in the art are also aware, rhodium is an expensive transition metal; and reducing the amount of rhodium used in the carbonylation process thus reduces the overall cost of the carbonylation process.

The rhodium-containing component of catalyst systems to which the instant invention has application includes those that are known and used in the prior art for carbonylation purposes—especially those used in carbonylation to produce acetic acid.

The rhodium-containing component of carbonylation systems to which the present invention has application may be provided by introduction into the reaction zone of a suitable compound of rhodium or of rhodium metal. Among the materials which may be charged into the reaction zone in this regard are, without limitation, rhodium metal, rhodium salts, rhodium oxides, rhodium acetates, organo-rhodium compounds, coordination compounds of rhodium and the like. Mixtures of such rhodium sources are also contemplated herein.

Specific examples of rhodium-containing components of catalyst systems to which the present invention has application include, without limitation: $RhCl_3$; $RhBr_3$; $RhI_3$; $RhCl_3 \cdot 3H_2O$; $RhBr_3 \cdot 3H_2O$; $RhI_3 \cdot 3H_2O$; $Rh_2(CO)_4Cl_2$; $Rh_2(CO)_4Br_2$; $Rh_2(CO)_4I_2$; $Rh_2(CO)_8$; $Rh(CH_3CO_2)_2$; $Rh(CH_3CO_2)_3$; $Rh[(C_6H_5)_3P]_2(CO)I$; $Rh[(C_6H_5P)]_2(CO)Cl$; Rh metal; $Rh(NO_3)_3$; $Rh(SnCl_3)[(C_6H_5)_3P]_2$; $RhCl(CO)[(C_6H_5)_3As]_2$; $RhI(CO)[(C_6H_5)_3Sb]_2$; $[Y][Rh(CO)_2X_2]$ wherein X=$Cl^-$, $Br^-$ or $I^-$; and Y is a cation selected from the group consisting of positive ions from Group IA of the Periodic Table of Elements, such as H, Li, Na, K, or Y is a quaternary ion of N, As or P; $Rh[(C_6H_5)_3P]_2(CO)Br$; $Rh[(n-C_4H_9)_3P]_2(CO)Br$; $Rh[(n-C_4H_9)_3P]_2(CO)I$; $RhBr[(C_6H_5)_3P]_3$; $RhI[(C_6H_5)_3P]_3$; $RhCl[(C_6H_5)_3P]_3$; $RhCl[(C_6H_5)_3P]_3H_2$; $[(C_6H_5)_3P]_3Rh(CO)H$; $Rh_2O_3$; $[Rh(C_3H_4)_2Cl]_2$; $K_4Rh_2Cl_2(SnCl_2)_4$; $K_4Rh_2Br_2(SnBr_3)_4$; $[H][Rh(CO)_2I_2]$; $K_4Rh_2I_2(SnI_2)_4$ and the like.

The present invention has preferred application to systems wherein the rhodium-containing component is $Rh_2(CO)_4I_2$, $Rh_2(CO)_4Br_2$, $Rh_2(CO)_4Cl_2$, $Rh(CH_3CO_2)_2$, $Rh(CH_3CO_2)_3$ or $[H][Rh(CO)_2I_2]$, with $[H][Rh(CO)_2I_2]$, $Rh(CH_3CO_2)_2$ and $Rh(CH_3CO_2)_3$ being most preferred.

In addition to rhodium, one can use other Group VIII transition metals comprising the iron triad, i.e. iron, ruthenium, osmium; the cobalt triad, i.e. cobalt, rhodium, as already discussed, iridium; or the nickel triad, i.e. nickel, palladium, platinum. Any of these will catalyze the carbonylation reaction, with the preferred metal, other than rhodium, being nickel.

In practice, the rhodium or other Group VIII metal concentration can vary over a wide range, although it is recognized that enough metal must be present to achieve reasonable carbonylation reaction rates; excess metal on the other hand may, on occasion, result in undesired by-product formation. The typical rhodium concentration in those carbonylation systems to which the instant invention has application is from about 200 to about 1200 ppm (about $2 \times 10^{-3}$ to about $13 \times 10^{-3}$ M). More preferably, the rhodium concentration is from about 400 to about 1000 ppm (about $4 \times 10^{-3}$ to about $10 \times 10^{-3}$ M). Although the foregoing concentrations, as stated, are for rhodium, these same levels apply to any of the other transition metals of Group VIII delineated above. The amount of rhodium or other Group VIII metal used is not a critical feature and higher concentrations are acceptable, subject to economic considerations.

As indicated above, the carbonylation process of the instant invention is carried out in the presence of a rhodium-containing component, as described above, and a liquid reaction medium which comprises water, methyl acetate, methyl iodide and acetic acid.

The concentration of water employed in carbonylation systems to which the instant invention relates is from about 0.01 to about 12 weight % (about $6.2 \times 10^{-3}$ to about 7.5 M). More preferably, the concentration of water employed in the carbonylation system is from about 4 to about 9 weight % (about 2.5 to about 5.6M). It should be noted that the concentration of water indicated above is generally considered by the art to be a so-called low level. This is distinguishable from prior art processes wherein water is provided in quantities which give a standing water concentration of 12 to 16% by weight or those that are run under anhydrous, i.e. no water, conditions.

Another component of the liquid reaction medium aspect of the carbonylation system to which the instant invention pertains is methyl acetate, which is charged into the reactor or formed in-situ in an amount of from about 0.5 to about 10 weight % based on the total weight of the liquid reaction medium. The foregoing weight % range of methyl acetate corresponds to a methyl acetate molarity of from about 0.07 to about 1.4 M. More preferably, the concentration of methyl acetate employed in the process of the present invention is from about 1 to about 8 weight % (about 0.14 to about 1.1 M).

A third component of the subject liquid reaction medium is methyl iodide ($CH_3I$), which can be added directly or formed in-situ by using HI, which reacts in-situ to form $CH_3I$. Typically, the concentration of $CH_3I$ employed in the instant invention is from about 0.6 to about 36 weight % (0.05 to about 3 M). More preferably, the concentration of $CH_3I$ employed in the instant invention is from about 3.6 to about 24 weight % (about 0.3 to about 2.0 M). When HI is employed, it is generally present in a concentration of from about 0.6 to about 23 weight % (0.05 to about 2.0 M). More preferably, the concentration of HI is from about 2.3 to about 11.6 weight % (0.2 to about 1.0 M).

The fourth component of the liquid reaction medium is acetic acid (HOAc), which is typically present in the reactor in an amount of from about 20 to about 80 weight %. The corresponding molarity range being from about 3 to about 12 M. More preferably, the amount of acetic acid that is charged into the reactor is from about 35 to about 65 weight % (about 5 to about 10 M).

An optional component of the carbonylation system is an alkali metal halide, e.g. LiI and/or LiBr, the iodide being more common place. It should be emphasized however that LiI is not required in the instant invention to achieve the results obtained hereinbelow in the examples. Thus, in one embodiment of the instant invention, LiI is not added to the liquid reaction medium.

When employed, LiI can be charged directly into the reactor or it can be formed in-situ by choosing lithium and iodine components that will result in the formation of LiI during the reaction. If LiI is employed, it is preferred to directly charge it into the reactor such that a concentration of from about 1 to about 20 weight % (about 0.1 to about 1.75 M) of LiI is present in the reactor. More preferably, this optional component is present in the reactor in an amount of from about 5 to about 10 weight % which corresponds to a molarity range of from about 0.5 to about 1.0 M.

Hydrogen may also be fed into the reactor to increase the overall rate of the carbonylation process. In this embodiment, improved carbonylation efficiency can be obtained when the addition of hydrogen to the reactor maintains a concentration of from about 0.1 to about 5 mole % $H_2$, based on the total number of moles of CO in the reactor. The preferred hydrogen addition is sufficient to maintain a concentration of from about 0.5 to about 3 mole % $H_2$ in the reactor. Hydrogen may be added to the reactor either as a separate stream or together with carbon monoxide; make-up amounts can be introduced in the same manner, as needed, to maintain the hydrogen concentration at the levels defined hereinabove.

In addition to the components mentioned hereinabove, a solvent or diluent may, optionally, be present. If a solvent or diluent is employed it is preferred that they be inert. The term "inert" as used herein means that the solvent or diluent does not interfere with the reaction to any significant extent. Illustrative examples of solvents or diluents that may optionally be used include, but are not limited to, 1,4-dioxane, polyethylene glycol diethers or diesters, diphenyl ether, sulfolane, toluene, carboxylic acids and the like. Mixtures of these inert solvents or diluents may also be present. Generally, the reaction is carried in the absence of any solvent or diluent other than those required to introduce reactants or catalyst components into the reactor.

The improved carbonylation process of the present invention can be carried out either in a batch or continuous mode. When operating in a continuous mode, the reaction system hardware usually comprises (a) a liquid phase carbonylation reactor, (b) a so-called "flasher", and (c) a methyl iodide-acetic acid splitter column. Other reaction zones or distillation columns may be present. Such hardware and the operation thereof are well known in the art. When operating in a continuous mode, the carbonylation reactor is typically a stirred autoclave within which the concentration of the reactants are maintained automatically at a constant level.

The carbonylation processes to which the instant invention relates is, for either mode, typically conducted under a pressure of from about 200 to about 1200 psig. More preferably, the carbonylation is conducted under a pressure of about 300 to about 600 psig.

The carbonylation processes to which the present invention relates is typically carried out at a temperature of from about 160° C. to about 220° C. More preferably, carbonylation is carried out at a temperature of from about 170° C. to about 200° C.

In practice, carbonylation reaction time varies, depending upon reaction parameters, reactor size and charge, and the individual components employed.

The experiments and examples detailed hereinbelow were carried out in a batch mode using a Hastelloy (trademark) C-276 stirred 300 ml autoclave. The reactor head was equipped with attachments for cooling coils, thermocouples and dip tubes for sample exit and return. Loss of vapor to the vapor stack was minimized by two in-series chilled water condensers.

The liquid reaction components, minus the catalyst, were then charged to the reactor. After leak testing with nitrogen and purging with CO, the reactor and its contents were heated to the desired temperature at a CO pressure of 100–200 psig with agitation.

The reaction was then started by injecting a chosen amount of a rhodium-containing catalyst into the reactor, following which the pressure of the reactor was raised to 400 psig. The reaction was allowed to proceed at constant pressure, which was maintained by feeding CO from a high pressure reservoir via a regulator. The extent of the carbonylation reaction was measured by the pressure drop in the reservoir. The pressure drop was converted to the moles of CO reacted using the known reservoir volume. At appropriate time intervals, infrared spectra were recorded to determine the active Rh(I) content using a Nicolet (trademark) 20DX spectrometer and liquid samples were removed for gas chromatographic analysis.

The liquid samples were analyzed using a Varian (trademark) 3400 Gas Chromatograph fitted with a 60 m×0.32 mm Nukol (0.25 micron film) capillary column. Gases were analyzed on-line using a Carle (trademark) series 400 AGC by opening a gas sampling valve and allowing the Carle sample valve to purge with reactor gas.

As stated above, improved carbonylation rates, product yields, and catalyst stability are obtained in the instant invention by incorporating at least one pentavalent Group VA oxide, preferably a phosphine oxide, as defined above, into the carbonylation system mentioned hereinabove. Unlike prior art processes, no alkali metal halides, e.g., LiI, are required in the practice of the instant invention wherefrom improved rates, yields and stability are provided. Moreover, the improvements herein ascribed to the use of pentavalent Group VA oxides are demonstrably superior to results obtained with prior art additives, such as phosphines and phosphates.

The following examples are given to illustrate the scope of this invention. Because these examples are given for illustrative purposes only, the present invention should not be limited thereto.

EXAMPLE 1

Effect of Pentavalent Group VA Oxides on Reaction Rate and Catalyst Stability This example compares the carbonylation rate and catalyst stability obtained in the practice of the present invention using $Ph_3PO$ as the pentavalent Group VA oxide and compares those results to the carbonylation rate and catalyst stability obtained using no additive.

In the experiment, the autoclave previously described herein was charged with 0.5 M HI, 0.7 M methyl acetate (MeOAc), 5 M $H_2O$ and, separately, with 1 M of $Ph_3PO$. The concentration of $Ph_3PO$ to rhodium was about 227:1. After leak testing with $N_2$ and purging with CO, the reactor was heated to 175° C. at a CO pressure of 175 psig.

Next, $4.4 \times 10^{-3}$ M $[H][Rh(CO)_2I_2]$ was injected into the reactor and the pressure was raised to 400 psig. The reaction was then allowed to proceed for up to about 1 hr.

The rate of acetic acid (HOAC) production was then determined by measuring the CO uptake and converting that data to moles of CO consumed. The production of acetic acid is a direct function of CO uptake and is plotted as a function of time.

The stability of the rhodium catalyst was then determined by plotting the concentration of the active rhodium species, in terms of Rh(I) mM, that remained in the reaction mixture as a function of time.

Figure 1B:
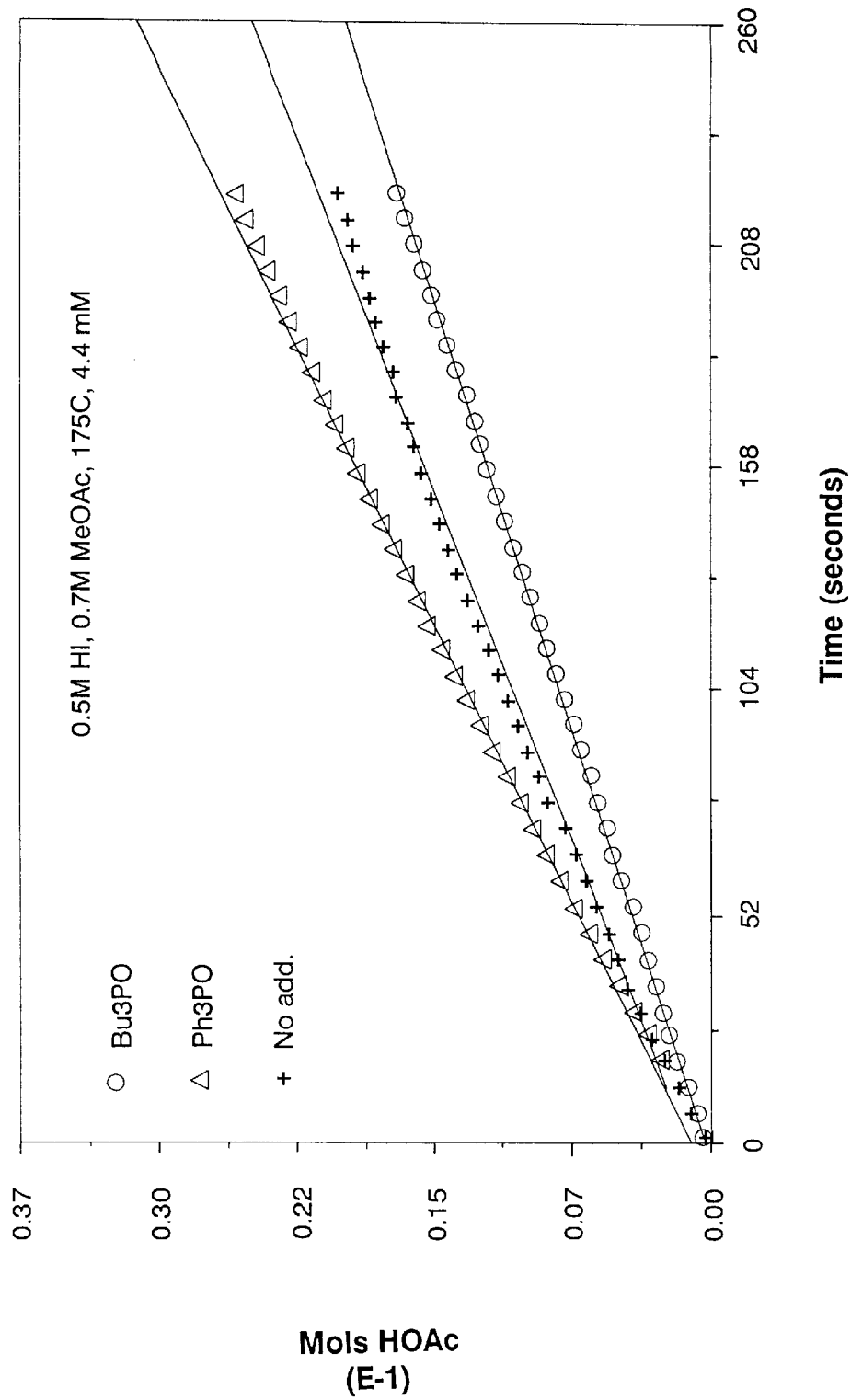
Figure 2:
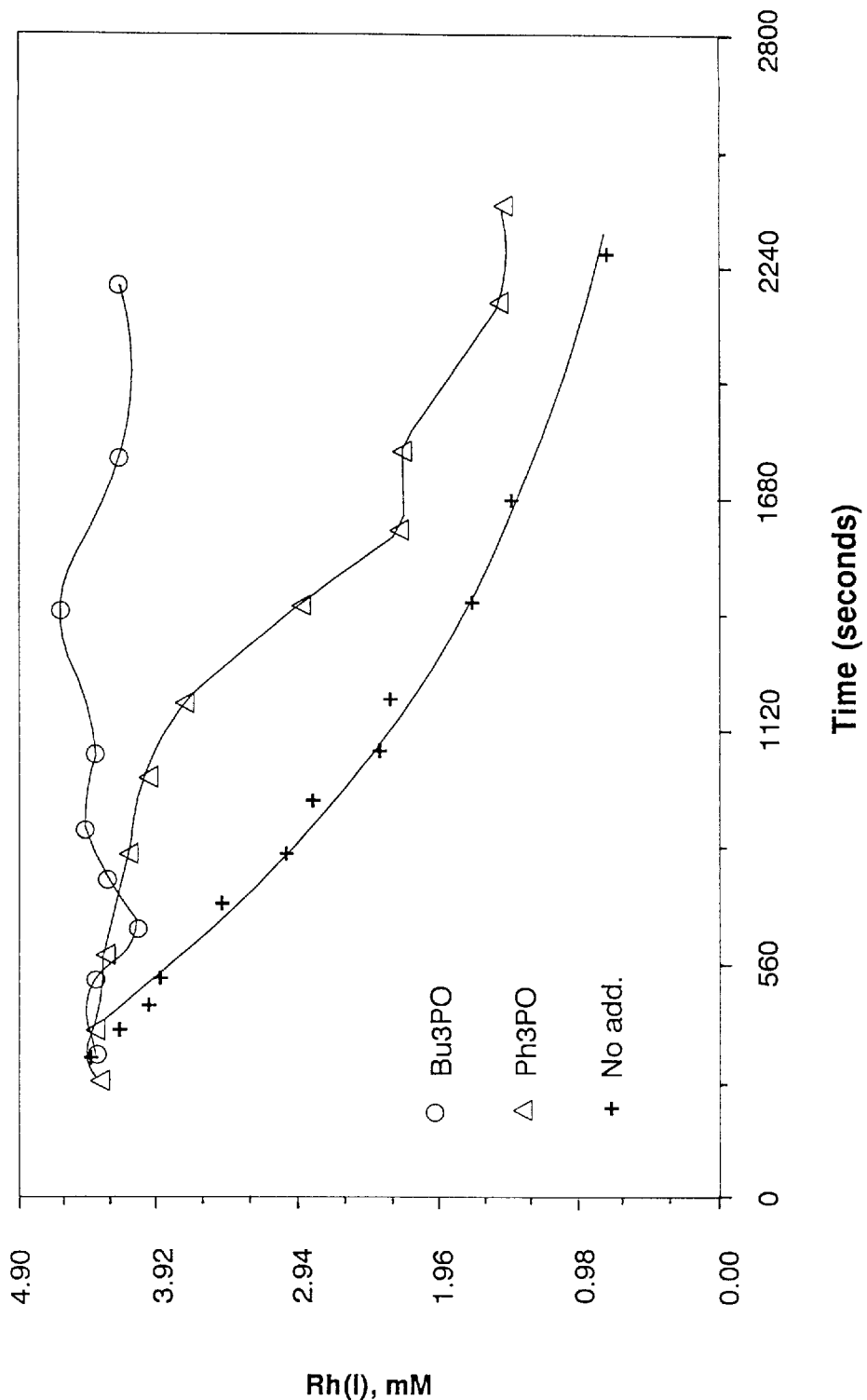
FIG. 2 is a graph showing the effect of various phosphine oxides on Rh(I) stability as exemplified in Examples 1 and 2.

The results of the foregoing experiments are shown in FIGS. 1 and 2. Specifically, as shown in FIGS. 1(a) and (b), the initial rate as well as the overall carbonylation rate was enhanced by employing $Ph_3PO$ in accordance with the present invention, as compared to the rate manifested where no additive at all was employed.

In regard to catalyst stability, FIG. 2 shows that the additive $Ph_3PO$ enhances the stability of the active Rh(I) species over a longer period of time as compared to the system wherein no additive was employed.

EXAMPLE 2

Effect of Pentavalent Group VA Oxides on Reaction Rate and Catalyst Stability This example compares the carbonylation rate and catalyst stability obtained in the practice of the present invention using $Bu_3PO$ as the pentavalent Group VA oxide and compares those results to the carbonylation rate and catalyst stability obtained using no additive.

This experiment was conducted using the reactants and the reaction conditions set forth in Example 1 except that 1 M $Bu_3PO$ was used as the additive. The concentration of $Bu_3PO$ to rhodium was also 227:1.

The results of the foregoing experiments are also shown in FIGS. 1 and 2. As is clearly shown in FIG. 1(a), an overall enhanced carbonylation rate was obtained by employing $Bu_3PO$ in accordance with the present invention, as compared to the rate manifested where no additive at all was employed.

In regard to catalyst stability, FIG. 2 shows that the additive, $Bu_3PO$, maintains catalyst stability over a much longer period of time as compared to the system wherein no additive was employed. This figure also shows that remarkably high catalyst stability can be obtained when $Bu_3PO$ is used as an additive instead of $Ph_3PO$. Thus, $Bu_3PO$ is used in instances wherein high catalyst stability is required.

EXAMPLE 3

Effect of Pentavalent Group VA Oxide Levels at Low Level Water Operation

This example shows the ability of the present invention, here using $Ph_3PO$ as the pentavalent Group VA oxide, to significantly enhance the carbonylation reaction and catalyst stability at low water concentrations. Specifically in this example, three carbonylation reactions were carried out according to the protocol described in Example 1, except for the following variations:

Run 1: 3 M $H_2O$; no additive

Run 2: 7 M $H_2O$; no additive

Run 3: 3 M $H_2O$; 1 M $Ph_3PO$

The concentration of $Ph_3PO$ to rhodium was 227:1.

Figure 3A:
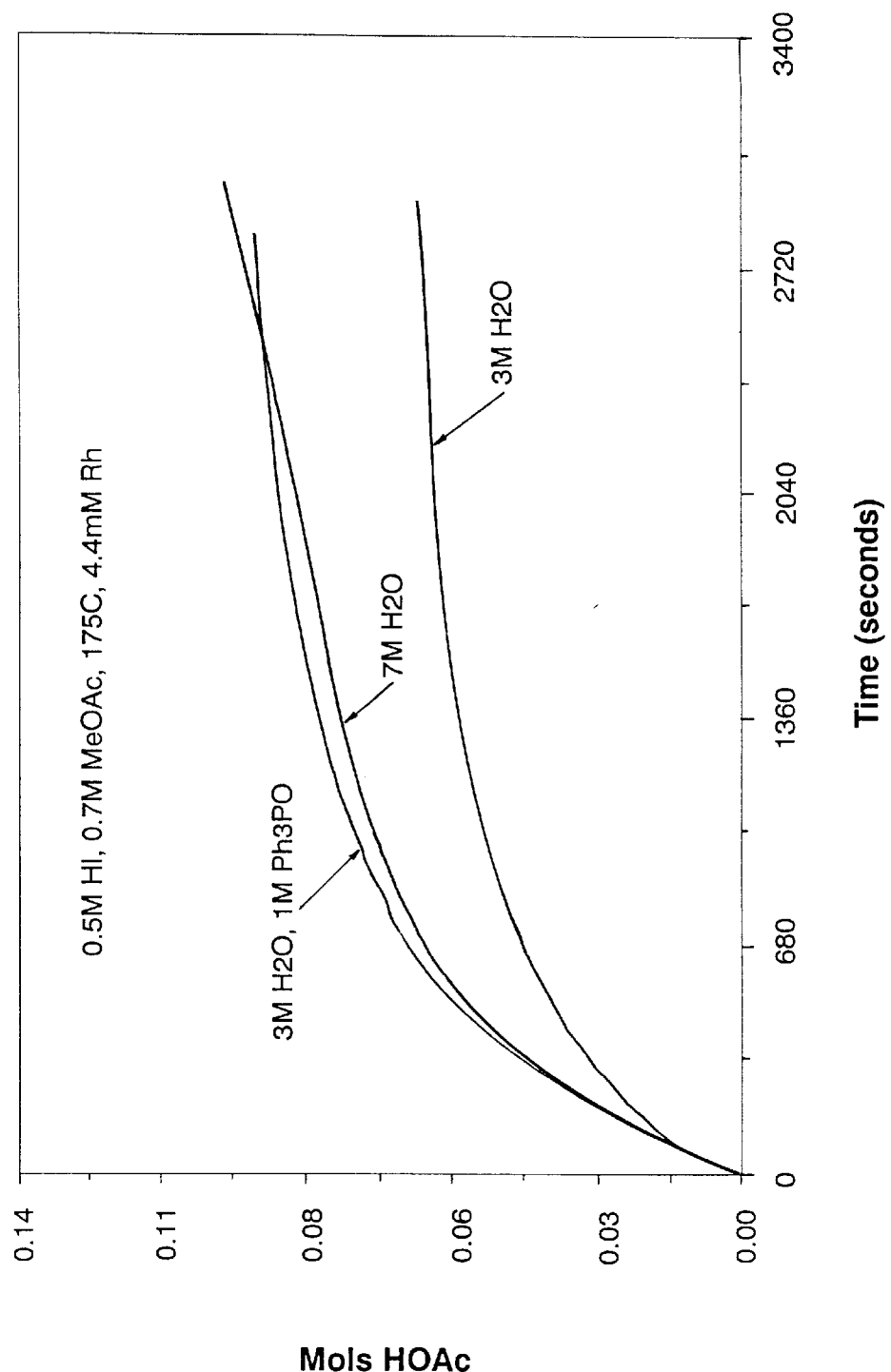
FIGS. 3(a) and (b) are graphs depicting the overall rate (a) and initial rate (b) of HOAc production at different water concentrations as exemplified in Example 3.
Figure 3B:
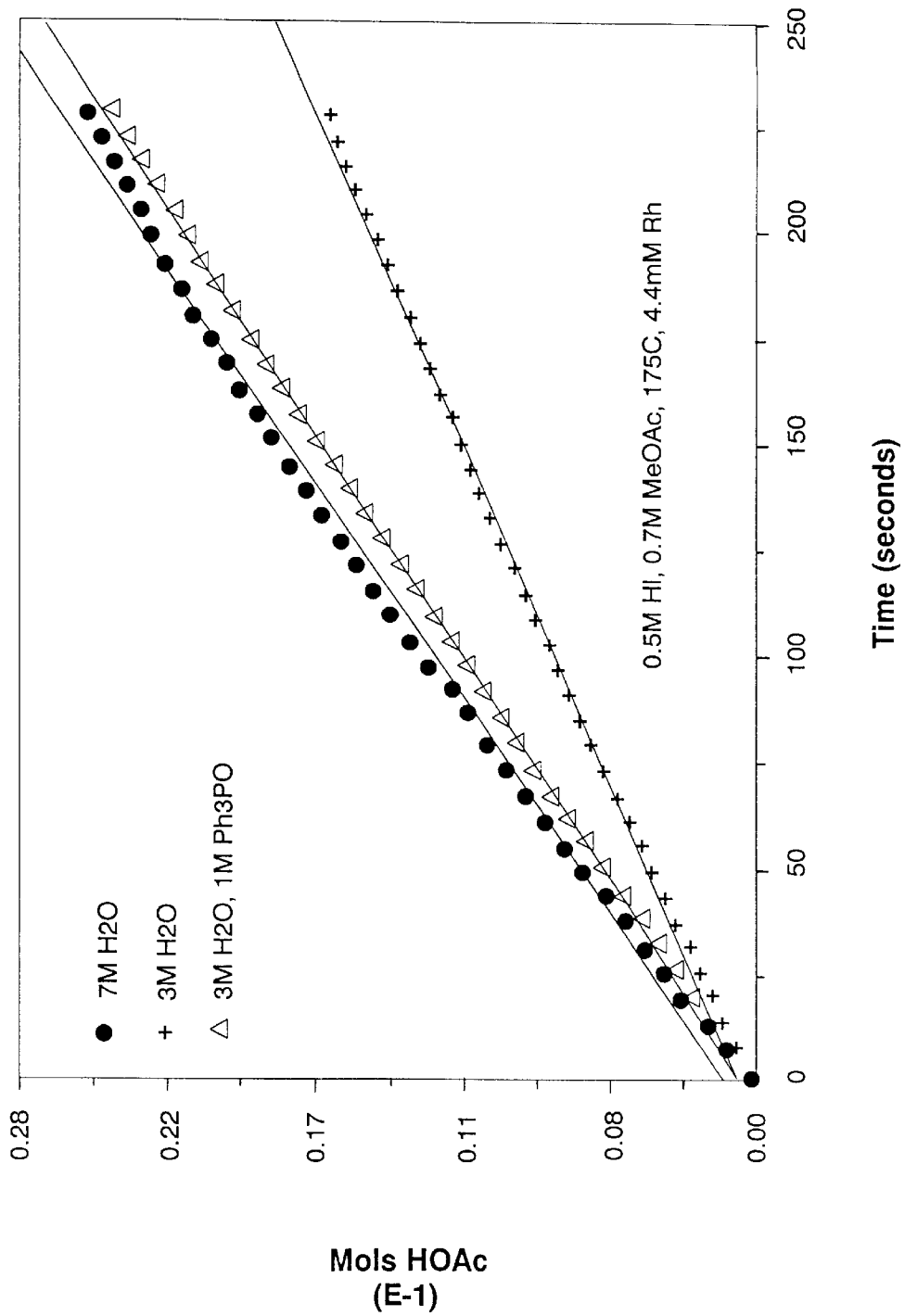

The carbonylation rates of this example are plotted in FIGS. 3(a) and (b). Specifically, the data in FIGS. 3(a) and (b) clearly show that the rate associated with a water level of 3 M wherein the present invention is employed (Run 3), here using $Ph_3PO$, is commensurate with the rate observed at a water level of 7 M $H_2O$ wherein no additives are employed (Run 2).

Figure 4:
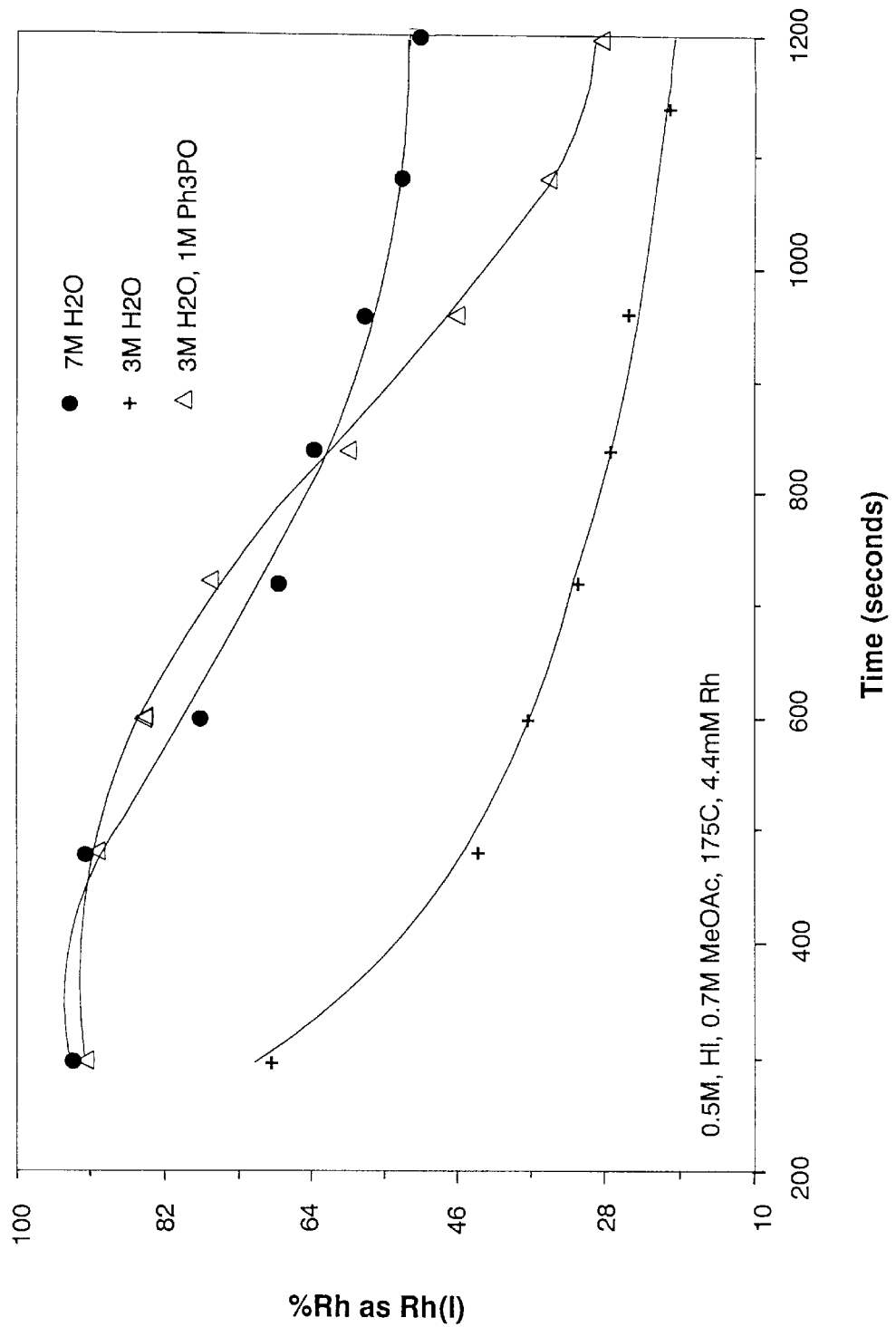
FIG. 4 is a graph showing the effect of $Ph_3PO$ on Rh(I) stability as exemplified in Example 3.

The ability to maintain catalyst stability using the above runs is plotted in FIG. 4. Specifically, this figure shows that the catalyst stability associated with a water level of 3 M using $Ph_3PO$ (Run 3) as an additive is commensurate with the catalyst stability observed at a water level of 7 M $H_2O$ wherein no additives are employed (Run 2). In other words, the additive of the instant invention restores the catalyst stability when operating at low water conditions; e.g. 3M, to a level which is obtained using a catalyst system wherein a higher amount of water (7 M) is present.

EXAMPLE 4

Effect of % Rh as Rh(I) an Initial Rate

The experiment in Example 1 was repeated except that the following reactants, in the amounts specified below, were charged into the reactor:

MeI: 1.3 M $Ph_3PO$: 0; 0.5; 1; and 1.5 M.

The respective $Ph_3PO$ to rhodium concentrations were 0; 114:1; 227:1 and 341:1.

Figure 5:
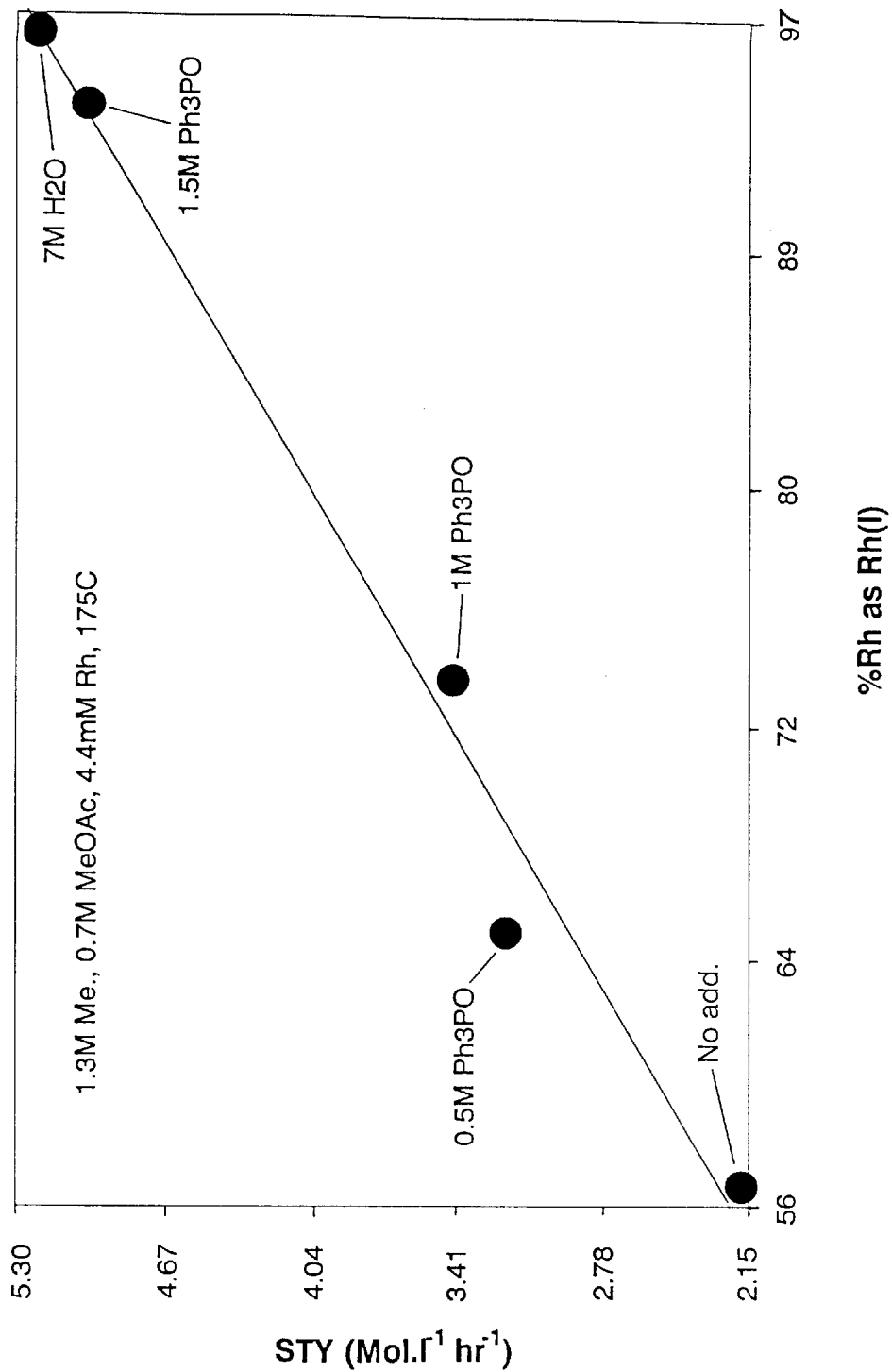
FIG. 5 is a graph of the initial rate of HOAc production, in terms of space-time-yield (STY), plotted against the % Rh as a Rh(I) species as exemplified in Example 4.

The results obtained from this experiment are plotted in FIG. 5. Specifically, the carbonylation rates, in terms of space-time-yield (STY) and expressed in moles $L^{-1}hr^{-1}$, were plotted as a function of the percent rhodium (% Rh) present as an active Rh(I) species. It is seen from this example that by increasing the concentration of $Ph_3PO$ and MeI a rate of 100% of the rate observed at 7 M $H_2O$, without additives, was obtained.

EXAMPLE 5

Comparative Effects of Phosphines, Phosphites and Pentavalent Group VA Oxides on Reaction Rate and Catalyst Stability This experiment was conducted to show that in the practice of the present invention using pentavalent Group VA oxides, exemplified herein using phosphine oxides, superior reaction rate and catalyst stability resulted, as compared to the reaction rates and catalyst stability associated with the use of phosphine or phoshite additives, as known in the art. In this example, methanol carbonylation was carried in accordance with the procedure described in Example 1 except that 3 M $H_2O$ and the additives listed in the following table were charged into the reactor. The additive concentration to rhodium in each run was 227:1.

| Run No. | Additive (1M) | Type | Reaction Rate (mol/l · hr) | Catalyst Stability % Rh as Rh (I) |
|---|---|---|---|---|
| 1 | none | — | 1.55 | 54 |
| 2 | $Ph_3PO$ | phosphine oxide | 2.25 | 93 |
| 3 | $(PhO)_3P$ | phosphite | 0.13 | 15 |
| 4 | $(MeO)_3P$ | phosphite | 0.71 | 35 |
| 5 | $(EtO)_3P$ | phosphite | 0.15 | 30 |
| 6 | $Bu_3P$ | phosphine | 0.08 | 0 |

Figure 6:
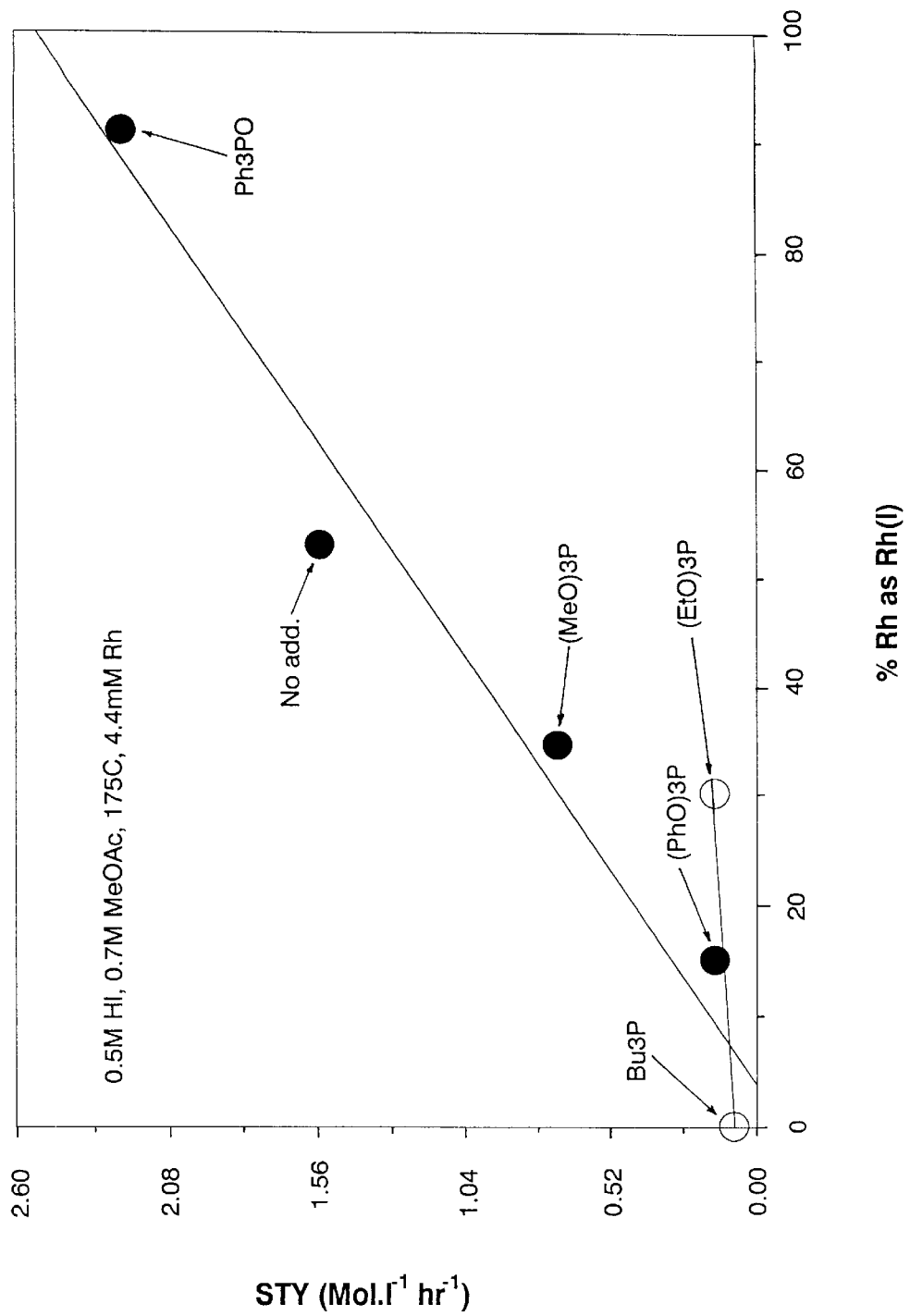
FIG. 6 is a graph showing the effect of initial Rh(I) on the initial rate of HOAc production using various phosphorus-containing additives at 3 M $H_2O$ as exemplified in Example 5.

As indicated in the foregoing table and as shown in FIG. 6, the use of a phosphine oxide ($Ph_3PO$) in accordance with the present invention (Run 2) provided an unexpectedly high reaction rate and catalyst stability as compared to the system wherein no additive was employed (Run 1) or systems wherein traditional phosphates (Runs 3, 4 and 5) or a phosphine (Run 6). This result is especially surprising since the prior art, such as U.S. Pat. No. 5,281,751 to Schreck, suggests that all such additives are interchangeable, and would thus behave similarly.

The above embodiments and examples are given to illustrate the scope and spirit of the present invention. These embodiments and examples will make apparent, to those skilled in the art, other embodiments and examples. These other embodiments and examples are within the contemplation of the present invention; therefore, the instant invention should be limited only by the appended claims.

What is claimed is:

1. In a process for producing acetic acid by reacting methanol with carbon monoxide in the presence of a carbonylation system containing a rhodium-containing component and a liquid reaction medium comprising water, acetic acid, methyl iodide, methyl acetate and an alkali metal halide and subsequently recovering acetic acid from the resulting reaction product, the improvement comprising:

introducing at least one pentavalent Group VA oxide of the formula:

$$R_3M=O$$

wherein M is an element from Group VA of the Periodic Table of the Elements; and each R is independently a substituted or unsubstituted alkyl, aryl, aralkyl or alkaryl, wherein any of which substituents of the carbon chains may be straight or branched or both, to the carbonylation system in an amount such that the concentration of said pentavalent Group VA oxide to rhodium is greater than about 60:1.

2. The process of claim 1 wherein said concentration of said pentavalent Group VA oxide to said rhodium is from about 60:1 to about 500:1.

3. The process of claim 2 wherein M is phosphorus and each R is independently a substituted or unsubstituted alkyl or aryl containing from about 1 to about 8 carbon atoms.

4. The process of claim 3 wherein at least one R is a substituted or unsubstituted phenyl.

5. The process of claim 3 wherein said pentavalent Group VA oxide is triphenylphosphine oxide or tributylphosphine oxide.

6. The process of claim 4 wherein said pentavalent Group VA oxide is triphenylphosphine oxide.

7. The process of claim 1 further comprising introducing hydrogen to said carbonylation system.

8. The process of claim 7 wherein said hydrogen is introduced in an amount sufficient to maintain a concentration of hydrogen of from about 0.1 to about 5 mole % $H_2$ in said reaction.

9. The process of claim 8 wherein said hydrogen is introduced in an amount sufficient to maintain a concentration of from about 0.5 to about 3 mole % $H_2$.

10. The process of claim 1 wherein said alkali metal halide is LiI.

11. The process of claim 10 wherein said LiI is present in a concentration of from about 1 to about 20 weight %.

12. The process of claim 11 wherein said LiI is present in a concentration of from about 5 to about 10 weight %.

13. The process of claim 1 further comprising introducing HI to said carbonylation system.

14. The process of claim 13 wherein said HI is present in a concentration of from about 0.6 to about 23 weight %.

15. The process of claim 14 wherein said HI is present in a concentration of from about 2.3 to about 11.6 weight %.

16. The process of claim 1 further comprising an inert solvent or diluent.

17. The process of claim 16 wherein said inert solvent or diluent is 1,4-dioxane, a polyethylene glycol diether, a polyethylene glycol diester, diphenyl ether, sulfolane, toluene, a carboxylic acid and mixtures thereof.

18. The process of claim 1 wherein said rhodium-containing component is $Rh_2(CO)_4I_2$, $Rh_2(CO)_4Br_2$, $Rh_2(CO)_4Cl_2$, $Rh(CH_3CO_2)_2$, $Rh(CH_3CO_2)_3$ or $[H][Rh(CO)_2I_2]$.

19. The process of claim 18 wherein said rhodium-containing component is $[H][Rh(CO)_2I_2]$, $Rh(CH_3CO_2)_2$ or $Rh(CH_3CO_2)_3$.

20. The process of claim 19 wherein said rhodium-containing component is present in amount of from about 200 to about 1200 ppm.

21. The process of claim 20 wherein said rhodium-containing component is present in an amount of from about 400 to about 1000 ppm.

22. The process of claim 1 wherein said water is present in a concentration of from about 0.01 to about 12 weight %.

23. The process of claim 22 wherein said concentration of water is from about 4 to about 9 weight %.

24. The process of claim 1 wherein said methyl acetate is present in an amount of from about 0.5 to about 10 weight %.

25. The process of claim 24 wherein said methyl acetate is present in an amount of from about 1 to about 8 weight %.

26. The process of claim 1 wherein said methyl iodide is present in a concentration of from about 0.6 to about 36 weight %.

27. The process of claim 26 wherein said methyl iodide concentration is from about 3.6 to about 24 weight %.

28. The process of claim 1 wherein said acetic acid is present in an amount of from about 20 to about 80 weight %.

29. The process of claim 28 wherein said acetic acid is present in an amount of from about 35 to about 65 weight %.

30. In a process for producing acetic acid by reacting methanol with carbon monoxide in the presence of a carbonylation system containing a rhodium-containing component and a liquid reaction medium comprising water, acetic acid, methyl iodide and methyl acetate and subsequently recovering acetic acid from the resulting reaction product, the improvement comprising:

introducing at least one pentavalent Group VA oxide of the formula:

R₃M=O wherein M is an element from Group VA of the Periodic Table of the Elements; and each R is independently a substituted or unsubstituted alkyl, aryl, aralkyl or alkaryl, wherein said alkyl is selected from propyl, isopropyl, isobutyl, t-butyl, amyl and hexyl;

said aryl is selected from β-naphthyl and aromatic rings of 14 carbon atoms;

said aralkyl has up to 16 carbon atoms wherein each aryl group thereof contains 6 to 10 carbon atoms and each alkyl group thereof contains up to 6 carbon atoms;

said alkaryl has up to 16 carbon atoms wherein each alkyl group thereof has 6 carbon atoms and each aryl group thereof has 6 to 10 carbon atoms;

or said pentavalent Group VA oxide is diphenylmethyl phosphine oxide;

to the carbonylation system in an amount such that the concentration of said pentavalent Group VA oxide to rhodium is greater than about 60:1.

* * * * *

UNITED STATES PATENT AND TRADEMARK OFFICE
CERTIFICATE OF CORRECTION

PATENT NO. : 6,031,129
DATED : February 29, 2000
INVENTOR(S) : James A. Hinnenkamp et al.

It is certified that error appears in the above-identified patent and that said Letters Patent is hereby corrected as shown below:

Title page,
Item [56], References Cited, FOREIGN PATENT DOCUMENTS, delete 2nd instance of "0097 978 A1 1/1998 European Patent Office" and; delete 2nd instance of "0 114 703 A1 8/1984 European Patent Office"

Signed and Sealed this

Twelfth Day of March, 2002

Attest:

Attesting Officer

JAMES E. ROGAN
Director of the United States Patent and Trademark Office